US012797629B2

(12) United States Patent
Morales Ruiz et al.

(10) Patent No.: US 12,797,629 B2
(45) Date of Patent: Nov. 17, 2026

(54) DEVICE FOR TRANSFERRING HEAT AND INFRARED ENERGY, WITH DYNAMIC TEMPERATURE CONTROL AND UNIFORM HEAT DISTRIBUTION

(71) Applicant: MACHINA INNOVATION LAB, S.A.P.I. DE C.V., Mexico City (MX)

(72) Inventors: Benjamín Alejandro Morales Ruiz, Mexico City (MX); Citlalli Jessica Trujillo Romero, Mexico City (MX); Luis Alberto Castellanos Rivera, Mexico City (MX); Edgar Alejandro Mandujano García, Mexico City (MX)

(73) Assignee: MACHINA INNOVATION LAB, S.A.P.I.DE C.V., Mexico City (MX)

( * ) Notice: Subject to any disclaimer, the term of this patent is extended or adjusted under 35 U.S.C. 154(b) by 662 days.

(21) Appl. No.: 17/628,760

(22) PCT Filed: Jul. 23, 2020

(86) PCT No.: PCT/MX2020/050022
§ 371 (c)(1),
(2) Date: Jan. 20, 2022

(87) PCT Pub. No.: WO2021/015607
PCT Pub. Date: Jan. 28, 2021

(65) Prior Publication Data

US 2022/0379135 A1 Dec. 1, 2022

(30) Foreign Application Priority Data

Jul. 24, 2019 (MX) .................... MX/a/2019/008765

(51) Int. Cl.
*A61N 5/06* (2006.01)
*A61F 7/00* (2006.01)

(52) U.S. Cl.
CPC ............ *A61N 5/0613* (2013.01); *A61F 7/007* (2013.01); *A61F 2007/0094* (2013.01);
(Continued)

(58) Field of Classification Search
CPC .......... A61N 5/0613; A61N 2005/0626; A61N 2005/0659; A61N 2005/0627;
(Continued)

(56) References Cited

U.S. PATENT DOCUMENTS 4,277,548 A * 7/1981 Vedder ................. H05K 3/0002 347/76
5,358,503 A * 10/1994 Bertwell .............. A61N 5/0616 606/2
(Continued)

FOREIGN PATENT DOCUMENTS

CN 204655815 U 9/2015
CN 208694050 U 4/2019
(Continued)

*Primary Examiner* — David Hamaoui
*Assistant Examiner* — Rumaisa Rashid Baig
(74) *Attorney, Agent, or Firm* — Reichel Stohry Dean LLP; Mark C. Reichel; Natalie J. Dean

(57) ABSTRACT

The present invention refers to a device to transfer heat and infrared energy with dynamic temperature control and homogeneous heat distribution that places one or more applicator modules on an affected area, later with a control module you can resort to a predefined therapy according to the affected area and some personal data of the patient, or to a therapy provided by the therapist, or even to set a temperature at which the device will heat up; the invention also refers to the manufacturing process of said device. The user can define the time interval that the therapy will last. Alternatively, the user may use a mobile application to control, monitor and personalize therapies, which he or his therapist may define from the mobile application or from a
(Continued)

web application, where said pair of applications will be connected to a web API for data synchronization.

18 Claims, 9 Drawing Sheets

(52) U.S. Cl.
CPC ................. *A61F 2007/0098* (2013.01); *A61N 2005/0626* (2013.01); *A61N 2005/0659* (2013.01)

(58) Field of Classification Search
CPC ................... A61N 5/0625; A61F 7/007; A61F 2007/0094; A61F 2007/0098; A61F 2007/0071; A61F 2007/0086; A61F 2007/0088; A61F 2007/0093
See application file for complete search history.

(56) References Cited

U.S. PATENT DOCUMENTS

| | | | | |
|---|---|---|---|---|
| 6,451,044 | B1 * | 9/2002 | Naghavi | A61F 2/86 623/1.42 |
| 6,471,716 | B1 * | 10/2002 | Pecukonis | A61C 19/06 606/9 |
| 6,569,189 | B1 * | 5/2003 | Augustine | A61F 7/007 602/41 |
| 6,602,275 | B1 * | 8/2003 | Sullivan | A61N 5/0616 607/90 |
| 8,900,283 | B2 * | 12/2014 | Johnson | A61N 5/06 607/90 |
| 9,367,822 | B2 * | 6/2016 | Shipon | G06Q 10/00 |
| D778,456 | S * | 2/2017 | Knaus | D24/209 |
| D989,970 | S * | 6/2023 | Liu | D24/209 |
| 2002/0143373 | A1 | 10/2002 | Courtnage et al. | |
| 2004/0044384 | A1 * | 3/2004 | Leber | A61N 5/0619 607/96 |
| 2004/0138726 | A1 * | 7/2004 | Savage, Jr. | A61N 5/0621 607/88 |
| 2005/0288748 | A1 * | 12/2005 | Li | A61F 7/007 607/98 |
| 2006/0287696 | A1 * | 12/2006 | Wright | A61N 5/0613 607/96 |
| 2007/0156208 | A1 * | 7/2007 | Havell | A61N 5/0616 607/88 |
| 2008/0183500 | A1 * | 7/2008 | Banigan | G06Q 10/10 705/3 |
| 2009/0205696 | A1 * | 8/2009 | Koester | H10N 10/13 136/201 |
| 2010/0324626 | A1 * | 12/2010 | Lefkovitz | A61N 5/0613 607/51 |
| 2012/0035689 | A1 | 2/2012 | Turtzo | |
| 2012/0256821 | A1 * | 10/2012 | Olsson | G06F 3/0338 345/156 |
| 2012/0306603 | A1 * | 12/2012 | Olsson | G06F 3/016 335/229 |
| 2014/0066507 | A1 * | 3/2014 | Manku | A61P 17/08 554/7 |
| 2014/0276248 | A1 * | 9/2014 | Hall | A61N 1/30 604/20 |
| 2014/0288351 | A1 * | 9/2014 | Jones | A61N 5/0624 607/90 |
| 2015/0018814 | A1 * | 1/2015 | Servell | A61N 5/00 606/33 |
| 2015/0112411 | A1 | 4/2015 | Beckman et al. | |
| 2015/0290028 | A1 * | 10/2015 | Isserow | A61F 7/007 607/109 |
| 2016/0015962 | A1 | 1/2016 | Shokoueinejad Maragheh et al. | |
| 2017/0080251 | A1 * | 3/2017 | Yehezkel | A61L 2/10 |
| 2017/0262604 | A1 * | 9/2017 | Francois | G16H 10/60 |
| 2018/0280720 | A1 * | 10/2018 | Tatsumura Hillyer | A61N 5/0619 |
| 2018/0305520 | A1 * | 10/2018 | Yang | B32B 25/10 |
| 2019/0000529 | A1 * | 1/2019 | Kothare | A61B 18/1402 |
| 2019/0047198 | A1 * | 2/2019 | Alemany Negrete | B29C 45/78 |
| 2020/0397611 | A1 * | 12/2020 | Simons | A61F 7/00 |
| 2021/0059601 | A1 * | 3/2021 | Taylor | A61F 7/0053 |
| 2021/0169682 | A1 * | 6/2021 | Alvarez | A61F 7/02 |
| 2021/0236328 | A1 * | 8/2021 | Popielarski | A61N 5/025 |
| 2021/0319872 | A1 * | 10/2021 | Valentine | G16H 40/67 |
| 2023/0165632 | A1 * | 6/2023 | Tunev | A61B 18/04 606/31 |
| 2024/0238650 | A1 * | 7/2024 | Roberts, II | A63B 24/0003 |

FOREIGN PATENT DOCUMENTS

| | | | |
|---|---|---|---|
| WO | 2011121481 | A1 | 10/2011 |
| WO | 2017175907 | A1 | 10/2017 |

* cited by examiner

DEVICE FOR TRANSFERRING HEAT AND INFRARED ENERGY, WITH DYNAMIC TEMPERATURE CONTROL AND UNIFORM HEAT DISTRIBUTION

TECHNICAL FIELD OF THE INVENTION

The present invention is related to the techniques and devices for transferring heat and/or infrared energy with dynamic temperature control and homogeneous heat distribution, in order to apply it in high precision needs and in particular for its use in therapies to reduce musculoskeletal pain (but not limited to these types of applications). The invention can be used domestically by inexperienced users, and also by all kinds of specialists in rehabilitation therapies against musculoskeletal pain. The invention can be used in a wide variety of places, from specialized rehabilitation centers and research centers, to the comfort of the homes of patients or users in general. In addition, the user can use it in any of the following body regions: neck, chest, abdomen, shoulders, back, extremities (arms, forearms, wrists, legs, feet, knees, ankles). It can be used in other industrial applications, whether or not they include therapies in living beings, which require precise temperature control and homogeneous heat distribution.

BACKGROUND OF THE INVENTION

Fundamentals

The World Health Organization reports that chronic and acute pain are considered a health problem worldwide. Between 20%-25% of the world's population suffers from some type of chronic pain. In Mexico, more than 28 million people suffer from chronic pain. Also, acute pain is considered as the main reason to attend the doctor. Musculoskeletal pain (muscles, ligaments or tendons) is considered one of the main reasons for disability to go to work. Therefore, pain not only has a negative impact on health, but also on the physical and emotional appearance of people. In addition, it also causes an economic impact in the country.

Drugs and thermotherapy are the most common treatments for pain. However, drugs cause various health effects. These are capable of generating physical dependence and causing withdrawal syndrome. In addition to causing various symptoms such as gastrointestinal damage, anxiety, irritability and even rapid heartbeat. On the other hand, thermotherapy is a therapeutic application of any substance that helps increase tissue temperature, blood flow, metabolism, and connective tissue extensibility. Blood circulation stimulates tissue recovery by providing the injury site with more oxygen, nutrients, proteins, etc., while metabolites and carbon dioxide are removed from the system. A 1° C. increase in local tissue is associated with a 10-15% increase in local metabolism. This change helps in the recovery process as it increases the catabolic and anabolic reactions necessary for metabolically degrading and removing products from the damaged area. In addition, the metabolism promotes the natural recovery process. In addition, thermotherapy modifies the temperature of the skin, activating thermo receptors that initiate nerve signals that block nociception (pain signaling process) within the spine. On the other hand, proprioceptors are also activated, they inhibit the transmission of nociceptor signals to the brain. Activating these receptors reduces muscle tone, decreases pain, and increases blood flow. [1-3].

Regarding the principles of action of infrared radiation, the literature describes it as a natural form of energy, which heats objects through a process called thermal radiation. The emitted infrared of 800-1200 nm is considered a form of energy that is not harmful to tissues. The energy penetrates the body up to 5 mm and has numerous effects on the skin and cells of the body and fat. There is the near infrared and the far infrared; however, the far infrared (FIR) is the only one capable of generating a thermal effect. Any person, when in contact with the FIR, experiences a form of heat. Because the primary source of infrared radiation is thermal radiation, any object with a temperature will radiate infrared. The hotter an object is, the more infrared radiation it will emit. Far infrared rays do not cause burns or damage to the skin. Infrared has two main uses: the first refers to domestic use (heating), and the second to the generation of infrared thermal therapies [4-6]. One of the advantages of infrared is that it increases blood circulation and oxygen supply to damaged tissues, promoting relaxation and comfort. In addition, it creates dilation in the vessels, which helps reduce blood pressure. The literature reports many other benefits of infrared, such as [7]:

Increased circulation and the formation of new capillaries: this helps transport more oxygen and nutrients to the injured area, speeding up the recovery process.

Increased phagocytosis: that is, it increases the cleaning of dead or damaged cells, including dead bacteria, improving the control of any infection process.

It stimulates the production of fibroblasts: these synthesize collagen, elastin and proteoglycans in the final healing phases.

It stimulates collagen production: it is the key protein involved in wound healing.

It increases the production of ATP (cellular energy): thus promoting the entire system in a faster regeneration [8,9].

Also, it has been used in: reducing inflammation, desensitizing nerves to pain, back pain, arthritis, sciatica, knee pain, neck pain, foot pain, joint pain, etc. Infrared light has been proven to relieve pain caused by muscle problems and joint stiffness. Infrared light penetrates deep into the skin, improving blood circulation and warming up the muscles. Furthermore, there are different techniques for LED arrays with which it is possible to construct either a uniform or personalized intensity distribution, and which could be used to generate adequate radiation patterns according to the area to be treated [10-12].

On the other hand, thermotherapy is a therapeutic application of any substance that helps increase body temperature, resulting in an increase in tissue temperature. Thermal therapy can be superficial or deep; this can generate analgesia and decrease muscle tone. With thermotherapy, tissue temperature, blood flow, metabolism, and connective tissue extensibility are increased [8, 13]. Thermal therapy can be generated through three mechanisms: conduction, convection, and conversion. Increased blood flow facilitates tissue recovery by providing protein, nutrients, and oxygen to the injury site. A 1° C. increase in tissue is associated with a 10-15% increase in local metabolism. Increased metabolism aids the recovery process by increasing the catabolic and anabolic reactions necessary to metabolically degrade and remove products of tissue damage and provide a means for tissue repair. Some studies have found that heating with a 40° C., pad placed on the skin of the lower back region achieves temperature increases of 5° C., 3.5° C. and 2° C. at depths of 19 mm, 28 mm and 38 mm, respectively. Heat from conductive heat treatment applied to knees of healthy subjects increases popliteal artery blood flow by 29%, 94%, and 200% after 35 minutes of treatment with a 38° C. heating pad, 40° C. and 43° C., respectively. Other research has shown that deep tissue blood flow increases by 27%, 77%, and 144% in the trapezoid muscle of healthy people when using a heating pad, with skin temperatures of 38° C., 40° C. and 42° C., respectively [4,5]. Blood circulation provides the organs with greater blood flow; therefore, the tissues obtain more oxygen, nutrients, and other vital components from the blood, while metabolites and carbon dioxide are removed from the system.

The greatest heating occurs in the skin and subcutaneous tissue within the first 5 mm below the skin's surface. In areas with adequate circulation, the temperature increases to its maximum after 6-8 minutes of exposure. Temperature increases at depths of 1 or 2 cm occur more slowly and require a longer exposure (15-30 min) to reach peak values [14,15]. After peak temperatures are reached, a plate-like effect or a small decrease in skin temperature can be observed for the remainder of the heat application [6]. Fat is considered an insulator and has a low thermal conductivity. Therefore, tissues under a large amount of fat are minimally affected by surface heating agents. Which is a problem with current devices.

The most used method in most homes to combat inflammation due to a muscle injury, or different problems with joints, is the use of hot compresses. Even high-performance athletes use this remedy for its high degree of effectiveness. However, the traditional procedure for applying such hot compresses, even in hospitals, is complicated and inefficient. This is because in some cases it is necessary to use a thermal bath that is regularly at a very high temperature to start therapy. Furthermore, it is impossible to keep the compress at a constant and uniform temperature throughout the therapy. Generally, since the compress is heated by means of the thermal bath, its temperature decreases after a few minutes after starting the treatment; this is due to the loss of heat due to the interaction of the pad with the environment.

There are some other techniques available for pain management and treatment. In the articles by E. García (2013) [16] and Gutiérrez (2013) [17] an analysis of different studies was carried out on the effectiveness of TENS devices for pain therapy, where the results were between inconclusive and with moderate evidence depending on the part of the body injured (knee, back, ankle, etc.). Deyo (2009) [18] published an article called "A controlled trial of TENS and exercise for chronic low back pain" in 2009 where he addresses the effectiveness of TENS in chronic low back pain. In this, unfavorable results were obtained for TENS; the main argument is that TENS is as effective as placebo in relieving this type of pain.

In 2009, Ingraham Paul [19], referenced different studies involving the use of ultrasound therapies. Here it is mentioned that the use of ultrasound in patients with low back pain is comparable with the placebo effect. In Ebadi S. (2014) [20], a study appears that is carried out on different scientific articles to determine the effectiveness of ultrasound in the treatment of the lower back and different results are obtained: the use of ultrasound generates a slight improvement. Furthermore, in the work of T. Watson (2015) [21], a complete study on the use of ultrasound in pain therapy is mentioned, where it is stated that the results depend on the use of the device, power and exposure. The use of ultrasound for the control and treatment of pain is not conclusive. However, it is a technology with high costs.

The article specialized in infrared therapies by P. Avci and his team (2013) [22], describes a study on laser therapies against inflammation and recovery from muscle injuries. The results obtained were in favor of the use of this technology. A dc-inflammatory effect was achieved and pain reduction in the injured area. On the other hand, in the study carried out by D. Gale and his group (2006) [4] 39 patients with low back pain were subjected to infrared light therapy, 21 patients were irradiated with far infrared radiation and another 18 received they treated with a placebo effect. The latter were fitted with the same device, however, it did not turn on. It was found that patients who were irradiated with infrared light did show improvement in their pain. Other works report that infrared penetrates the body up to 5 mm and has numerous effects on skin and body cells and fat [3]. The benefits are mainly, increased circulation, stimulation of fibroblast production, etc. [7.9].

The article by Dehghan (2014) [23] on thermotherapy, compares the use of heat and cold in order to find which is more effective in generating an analgesic effect against low back pain. The two therapies were effective, however, with thermotherapy a more accelerated reduction of pain was obtained than with cryotherapy. When the skin is heated there is also a heating of the tissue which leads to an amplification of the blood vessels. The therapeutic effect is based on the improvement of local blood circulation. Blood circulation provides organs with blood, therefore, tissues obtain more oxygen, nutrients, and other vital components from the blood, while metabolites and carbon dioxide are removed from the system.

There were dozens of products currently available on the market focused on solving the problem mentioned here. Among them, 4 common technologies were distinguished, on which the analysis was based:

TENS. For its acronym in English Transcutaneous Electrical Neuro Stimulation, consists of electrical stimulation through electrodes that are placed in the affected area. This technology has been in the market for more than 30 years and in recent years its use has been extended by the wide range of products from Asian manufacturers. This is one of the most popular technologies in the field of rehabilitation. Despite its great popularity, it has been shown that its degree of effectiveness for the treatment of pain is nil, numerous clinical studies indicate that the effect generated in the body is merely placebo, and there is no evidence that shows regenerative effects in the affected area.

Ultrasound. It works by means of mechanical waves at frequencies that are imperceptible to the human ear. The basic principle is to stimulate the damaged muscle. This technology is rare and often expensive.

Thermotherapy. The use of this technology consists of applying heat by means of hot or cold compresses, thermal gel bags, seed bags and in some cases heat patches. As mentioned before, this is the most common method of therapy. This heating has the function of dilating the blood vessels, increasing the flow of blood in the body. This speeds up the natural recovery process.

Infrared light. It is applied by using incandescent lamps, LED light lamps or by LASER. Infrared radiation is a natural form of energy, which heats objects through a process called thermal radiation. The emitted infrared of 800-1200 nm is considered a form of energy that is not harmful to tissues. The energy generated by infrared light penetrates the epidermis, reaching the dermis (up to 5 mm below the epidermis) and has numerous effects on the skin and cells of the body and fat.

Representative Products

Next, 6 of the most representative products are mentioned according to the use of their main technology and that are very easy to acquire:

COMPEX WIRELESS: it is a TENS device aimed at sportsmen and high performance athletes. His focus is not rehabilitation but muscle activation before and after physical activity. This device has a digital display, rechargeable battery and APP for mobile devices. The most complete version of this device is wireless and can be purchased directly from its website and other online shopping sites.

LIVIA: this is a TENS device specifically targeted at the female market. This product was made with the aim of relieving menstrual cramps. This was funded through crowdfunding platforms such as IndieGogo and Kickstarter. The device has an attractive design, portable and easy to use. Currently, it can be purchased through its website.

LUMIWAVE: is an LED light therapy device that is aimed at the user who suffers from any kind of muscle pain. This device has two presentations according to the size of the area to be treated. The first presentation is to treat small areas of the body (ankle, knee, wrist etc), while the second is to treat areas of greater surface (back, leg). This device can be purchased through their website.

iTENS: This is a TENS device against muscle pain. Its design allows it to be used in different parts of the body. It has a mobile application that helps to control the device and keep track of therapies. Through their website you can buy the device and spare parts.

VENTURE HEAT WRAP: it is a thermotherapy product and the difference it presents with other products is that it uses an accessory for each part of the body, be it elbows, knees, ankles, etc. This has a temperature control and rechargeable battery. The different devices can be purchased directly on their website.

THERASAGE: this is a device that makes use of thermotherapy. This product works by means of infrared radiation generating heat in the required area. It is sold in different sizes depending on the area to be covered, with the wrist being the smallest area and the back being the largest. It is not very efficient since it is not designed with an ergonomic aspect, which makes it difficult to cover certain areas of the body and therefore the energy waste is greater. It can be purchased on the product's website or on different online shopping platforms.

RELATED PATENTS

Listed below are patents found on LED or infrared light emitting devices for pain treatment:

On the other hand, patent US 200210143373 A1 [24] in the name of Peter A. Courtnage, Robin E. Schaffer registered on Jan. 25, 2002, talks about a generic system and method for the therapeutic application of energy. The energy is applied by means of photon emitting diodes in combination with transcutaneous electrical stimulators, which he calls energy sources. In addition, there is a memory-retention moldable housing that contains the power sources and the electrical network.

US patent 2003/6,569,189 B1 [25] in the name of Scott D. Augustine et. al., describes a tissue treatment apparatus that include: a bandage that is transparent or transmits energy in a range between the wavelengths between 3 and 30 nm of the infrared (IR) portion of the electromagnetic spectrum. A heater is used to generate heat, including IR radiation, and a fixation device holds it over the band-pass bandage layer. The bandage and warmer together have a profile that allows them to conform to the shape of a wound and to the contours of the skin near the wound. In addition, a controller can be provided to cycle the temperature of the heater to maintain the normothermic condition.

Patent US 2016/0015962 [26] refers to a flexible patch that is capable of emitting light in the UV, visible and/or infrared electromagnetic spectra. The patch contains a feedback process and a system that uses one or more sensors and a controller in the patch to: (1) speed up the wound healing process by providing adaptive and controlled light exposure, and (2) monitor the healing process for signs of infection (3) eliminate bacterial infections by disinfecting the infected site and (4) transmit the information wirelessly to a central location for a physician to store and interpret, as well as providing the ability to receive comments and operating instructions from the physician from a remote location.

US 2004/0044384 [27] describes an energy therapy device that uses a series of energy emitting elements to stimulate the flow of energy along the acupuncture meridians. The elements that emit energy are turned on and off sequentially to produce an energy wave. The energy wave is brought into contact with, or very close to, anatomical sites on a patient's body that have underlying acupuncture meridians. The energy wave produced by the energy therapy device stimulates the flow of energy resulting in a number of therapeutic benefits including pain relief and reduction of inflammation.

Differentiation

The invention presented here has similar aspects with each of the patents mentioned, in some cases the most similar aspect is the application, but not the method or technology, in others there are similar components, but as will be seen in the description of Our invention, it is not possible from these patents to infer a technology similar to ours in its engineering, applicability and inventive activity.

The application of thermal and infrared technologies in problems that require high reliability and efficiency (as in the case of health problems and in particular pain therapy), requires an understanding of the state of the art in the matter (exposed in the first part of the background of the invention) and the determination of the engineering of the invention described here is the result of a process of research and laboratory tests that allow to define with precision the technical characteristics of the thermal modules, the calibration and control process dynamic temperature, and the manufacturing process that solves many final product integrity problems, and for which there are no similar processes in the industry.

There are no tools in clinical practice that, according to the scientific information collected on the effect of thermal therapies on the body, allow efficient therapy against musculoskeletal pain, a method of therapy is not found in the scientific literature that we can use in our device, this is the main problem that our invention solves. It will provide a specialist with an efficient tool for the research and design of new thermal therapies against musculoskeletal pain. Our invention is not a method to give any type of therapy and can be used in other non-medical applications that require dynamic control and efficient heat distribution.

BIBLIOGRAPHY

[1] Tepperman P. S, Devlin M., "The therapeutic use of local heat and cold", Can. Fam. Physician, vol. 32, no. 5, pp. 1110-1114, 1986.

[2] Fernández-Carvajal A et al. Review: "New strategies to develop novel pain therapies: Addressing thermoreceptors from different points of view", Pharmaceuticals, vol. 5, no. 1, pp. 16-48, 2012.

[3] Dubin A, Patapoutian A., Review series “Nociceptors: the sensors of the pain pathway”, J. Clin. Invest., Vol. 120, no. 11, pp. 3760-3772, 2010.

[4] Gale G D, Rothbart P J, Li Y., “Infrared therapy for chronic low back pain: A randomized, controlled trial”, Pain Res. Manag., Vol. 11, no. 3, pp. 193-196, 2006.

[5] Lin C C, et al., “Far-infrared therapy: a novel treatment to improve access blood flow and unassisted patency of arteriovenous fistula in hemodialysis patients”, J. Am. Soc. Nephrol., Vol. 18, no. 3, pp. 985-992, 2007.

[6] Anderson M K, Parr G P, “Foundations of athletic training: prevention, assessment, and management”, section 2, 4th ed.; 2006.

[7] Logicor (CH) Ltd, “Health benefits of far infrared”, 2014.

[8] Putowski M. et al., “The use of electromagnetic radiation in the physiotherapy”, Eur. J. Med. Technol., Vol. 2, no. 11, pp. 53-58, 2016.

[9] Hawkins D., Abrahamse H. “Phototherapy—a treatment modality for wound healing and pain relief”, vol. 10, pp. 99-109, 2007.

[10] Moreno I., Avedaño A M, Tzonchev R I, “Designing light-emitting diode arrays for uniform near-field irradiance”, Applied Optics, Vol. 45, No. 10, p. 2265-2272, 2006.

[11] Sourav P., “Optimization of LED array for uniform illumination over a target plane by evolutionary programming”, Optical Society of America, vol. 54, No. 27, p. 8221-8227, 2015.

[12] Praneth V G V S S, Sushma R., Sharma V., Kumar A., Sharma G V V, “Power allocation for uniform illumination with stochastic LED arrays”, Vol. 25, No. 8, p. 8659-8669, 2017,

[13] Nadler S F, Weingand K., Kruse R J, “The physiologic basis and clinical applications of cryotherapy and thermotherapy for the pain practitioner”, vol. 7, no. 3, pp. 395-399, 2004.

[14] Garra G., et al. “Heat or cold packs for neck and back strain: a randomized controlled trial of efficacy”, Society for Academic Emergency Medicine, vol. 17, no. 5, pp. 484-489, 2010.

[15] Mordeniz C., “Pain perception within consciousness”, NeuroQuantolog vol. 14, no. 2, pp. 439-446, 2016.

[16] García R., Márquez S., Gómez R., Beltrán C., “Eficacia, seguridad y coste-efectividad de la estimulación nerviosa eléctrica transcutánea (TENS) en el tratamiento del dolor musculoesquelético crónico”, Informes de Evaluación de Tecnologías Sanitarias, Agenda de Evaluación de Tecnologías Sanitarias de Andalucía, 2013.

[17] Gutiérrez H., González P., Gellona R., “Onda corta para el dolor musculoesquelético. Revisión sistemática”, Rev. Soc. Esp. Dolor, vol. 20, no. 5, pp. 230-262, 2013.

[18] Deyo R A, Walsh N E, Martin D C, Schoenfeld L S, Ramamurthy S., “A controlled trial of transcutaneous electrical nerve stimulation (TENS) and exercise for chronic low back pain”, The N. Engl. J. of Med., 322: 1627-1634, 1990.

[19] Ingraham P., 2009, https://www.painscience.com/

[20] Ebadi S., Henschke N., Nakhostin A N, Fallah E., Van Tulder M W, Review “Therapeutic ultrasound for chronic low-back pain”, Cochrane Database of Syst. Rev., 2014.

[21] Watson, T. and S. Young (2008). Therapeutic Ultrasound. Electrotherapy: Evidence Based Practice. T. Watson. Edinburgh, Churchill Livingstone, Elsevier.

[22] Avci P., Gupta A., Sadasivam M., Vecchio D., Pam N., Hamblin M R, “Low-level laser (light) therapy (LLLT) in skin: stimulating, healing, restoring”, Semin. Cutan. Med. Surg., 32 (1), pp. 41-52, 2013.

[23] Dehghan M., Farahbod F., “The efficacy of thermotherapy and cryotherapy on pain relief in patients with acute low back pain, a clinical trial study”, J. Clin. Diagnost. Res., 8 (9), 2014.

[24] US patent 2002/0143373 A1, “System and method for therapeutic application of energy”, Oct. 3, 2002.

[25] US patent 2003/6569189 B1, “Tissue treatment apparatus including a bandpass filter transparent to selected wavelengths of IR electromagnetic spectrum”, May 27, 2003.

[26] US Patent 2016/0015962, “Smart patch for wound management”, Jan. 21, 2016.

[27] US Patent 2004/0044384, “Therapeutic method and apparatus”, Mar. 4, 2004.

DESCRIPTION OF THE INVENTION

DETAILED DESCRIPTION OF THE INVENTION

Figure 1:
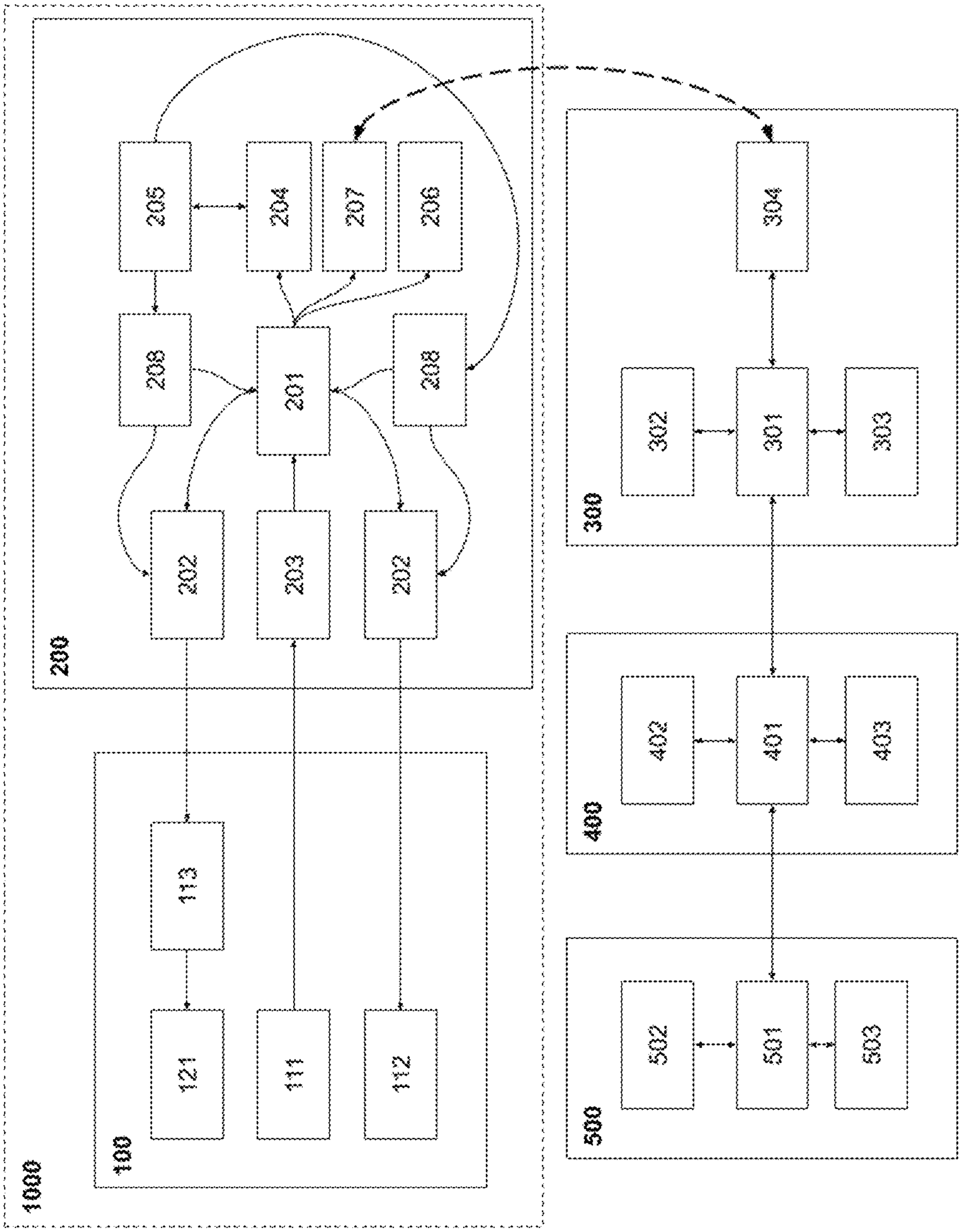
FIG. 1 is a block diagram showing the different modules that make up the therapeutic device against musculoskeletal pain of the present invention.

The present invention relates to a device for transferring heat and infrared energy with dynamic temperature control and homogeneous heat distribution [1000] with dynamic temperature control and homogeneous heat distribution, and a means for its application. The therapeutic device against musculoskeletal pain described here includes 5 modules as illustrated in FIG. 1 and which are described below:

1. Applicator module (example heating pad) [100]: this module is in direct contact with the user and consists of a flexible pad made of an elastomer for clinical use that serves as an encapsulation for the electronic components necessary to deliver the therapy. The applicator module encapsulates in its interior the actuators responsible for supplying the thermal and infrared energy, the sensors for temperature measurement, as well as the appropriate components to limit the maximum temperature that could be generated by a failure or improper use of the device. It also contains a series of support elements that give physical integrity to all the instrumentation and all the modules inside, and it contains a multiple connector for a plurality of power and communication cables.

2. Control module [200]: it is in charge of managing the energy that flows to the thermoelectric grid and the infrared LEDs, monitoring and controlling the temperature of the applicator module in real time, controlling the operating time, providing an interface with the user by means of a screen and various buttons, to store and transfer all relevant data on the use and operation of the applicator module and the control module, as well as allowing to establish a wireless connection to a remote interface, which can be a mobile application (not limited to this type of technology). It contains all the instrumentation necessary to carry out these functions, as well as the batteries that supply the energy for its operation and for the applicator module, as well as a system for charging them. This device is capable of processing a variety of predefined commands in the Microcontroller Firmware, CPU, or any other type of programmable digital device that is used for that purpose. This device will also have the ability to perform integrity tests (measurement of currents, voltages, elevation and adequate measurement of temperatures), as well as the calibration of the Applicator Modules [100] used, in order to guarantee repeatability in its use with other Control modules. The control module also contains three connectors that allow controlling the same number of applicator modules 100.

Additionally, the device can interact with the following three modules that are described below, which are focused on the development of thermal therapies against musculoskeletal pain, but are not limited to this type of application:

3. Mobile application module [300]: the mobile application module connects via Bluetooth to the control module, and can fulfill the following functions: (a) access all the information on the use of the applicator module and the control module, (b) perform functional tests and calibration of the modules, (c) serve as an interface to the user to execute all the functions that can be carried out performed on the control module, (d) configure and modify control module functions. The mobile application module also serves to safeguard a user file, and facilitate the monitoring of the efficiency of the therapeutic device for all the uses it is given, and compare it with a database of other users.

4. Web Application Interface Module (Web API) [400]: The modules of the mobile application of different users can be connected asynchronously via the Internet to the web API module to synchronize the therapy data of said users of the system. Personalized information can also be sent to each user through the web API. Another of the functionalities is to allow the connection with third-party applications or with programs that allow the expansion of their functionalities or applications.

5. Web application module [500]. This module connects via the internet to the web API and contains a user interface so that the user of the system or therapist can send messages, consult therapy history, consult therapy statistics either for a user or for all users of the system. registered in the web API, analysis of information about the integrity and calibration of the Applicator Modules, statistics on benefits evaluated through questionnaires applied to users, effectiveness of therapies, and in general analysis of the data collected by the Mobile application module, among other types of information display that may be useful in the user's pain therapy.

Referring to the accompanying drawings, in FIG. 1, the 2 modules of the system for pain therapy constructed according to an embodiment of the present invention are shown, which should be considered as illustrative but not limiting thereof, additionally the figure shows the additional modules that complement the use in therapies for musculoskeletal pain. The system broadly comprises the following modules: an applicator module [100], a control module [200], a mobile application module [300], a web application programming interface module [400], a web application [500].

The applicator module [100] in the preferred embodiment of the invention, contains two actuators in charge of providing the energy that will be used for the treatment of pain. The two actuators mentioned are a heating layer [120], which is a thermoelectric mesh, and a component that is an array of infrared LEDs [110], which in the case exemplified are LEDs (Light-Emitting Diodes) infrared light emitters of a wavelength in a range between 800 nm and 1200 nm. The distribution of the LEDs in the applicator module was designed according to the models and optimization methods referenced in the antecedents to propose the spatial distribution over the entire area that makes up the applicator module that generates a uniform intensity pattern or even patterns that are tailored to specific area applications on the body.

The applicator module [100] also contains several temperature sensors [111] distributed within the applicator module. Said temperature sensors [111] will allow the control module [200] to know the temperatures in real time at various points within the applicator module [100] which will allow the control module [200] to manage the energy supplied to the heating layer [120] to keep the specific temperature of each therapy balanced. The applicator module [100] has a safety-thermoelectric component [113], which prevents the heating module [121] from exceeding the maximum allowed temperature, this will allow the electrical circuit to be opened, interrupting the flow of energy to avoid overheating, thereby which can happen in case of misuse of the applicator module. The applicator module [100] can include, in front of the area of contact with the user, a series of visual elements, for example, one or more colored LEDs, for visual feedback from the user or even some type of auditory feedback by middle of a buzzer.

Figure 2A:
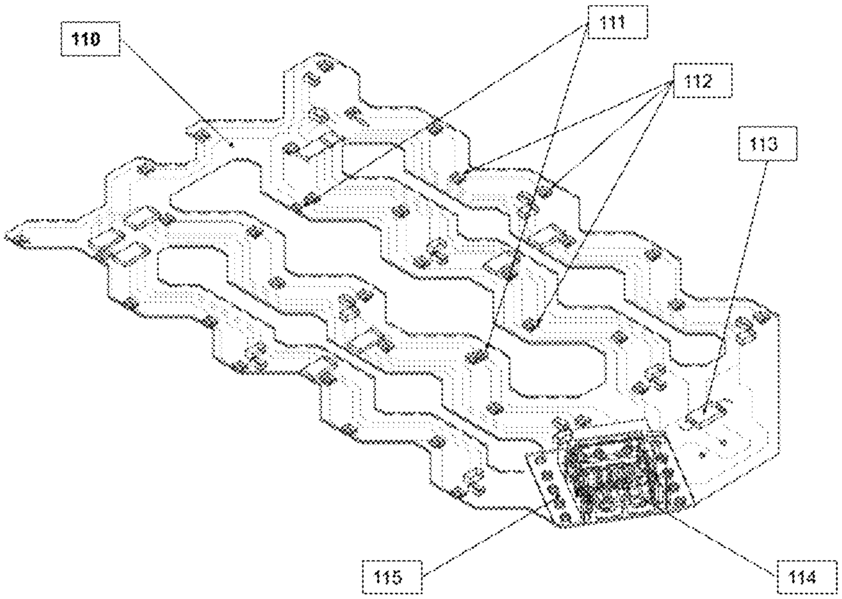
FIG. 2*a* is a perspective view of the PCB (Printed Circuit Board) [110] that contains the following components: the temperature sensors [111], the instrumentation of the infrared power generation system [112], the component thermoelectric safety device [113] and the multiple connector, which connects the electrical connection tracks for the mentioned components, as well as for the heating module [120].

The FIG. 2*a* shows the PCB (Printed Circuit Board) [110] that contains the following components: the temperature sensors [111], the instrumentation of the infrared power generation system [112], the thermoelectric safety component [113] and the multiple connector, which connects the electrical connection tracks for the aforementioned components, as well as for the heating module [120]. The infrared emitter [112] is composed of elements for converting electrical energy to electromagnetic radiation energy at the infrared wavelength, which in our case is in the range from 800 nm to 1200 nm. The PCB module is made of a flexible material (for example Kapton) and contains a more rigid preform [115] that works as a protector for the multiple connector and was developed with structural elements that allow ensuring the integrity of all the components that are joined to the connector.

Figure 2B:
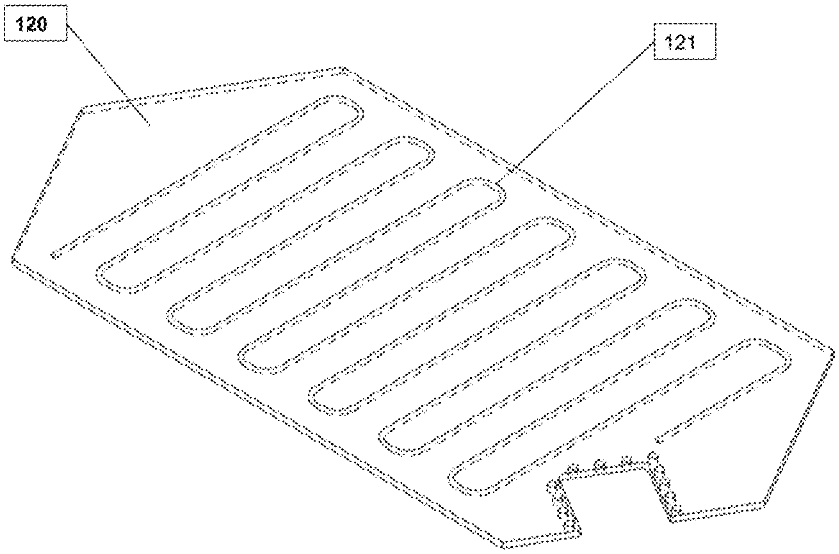
FIG. 2*b* shows the heating module [120], which is composed of a resistance mesh [121] woven over a wire mesh, which has high porosity to allow bonding with the elastomer that forms the core [140] of the applicator device [100].

FIG. 2*b* shows the heating module [120], which is composed of a resistance mesh [121] woven over a wire mesh, which has high porosity to allow bonding with the elastomer that forms the core [140] of the applicator device [100]. The resistance mesh shown in the figure is illustrative, but does not show the precise parameters used in the manufacture of the product, which were defined based on experiments to achieve the required heat flow.

Figure 2C:
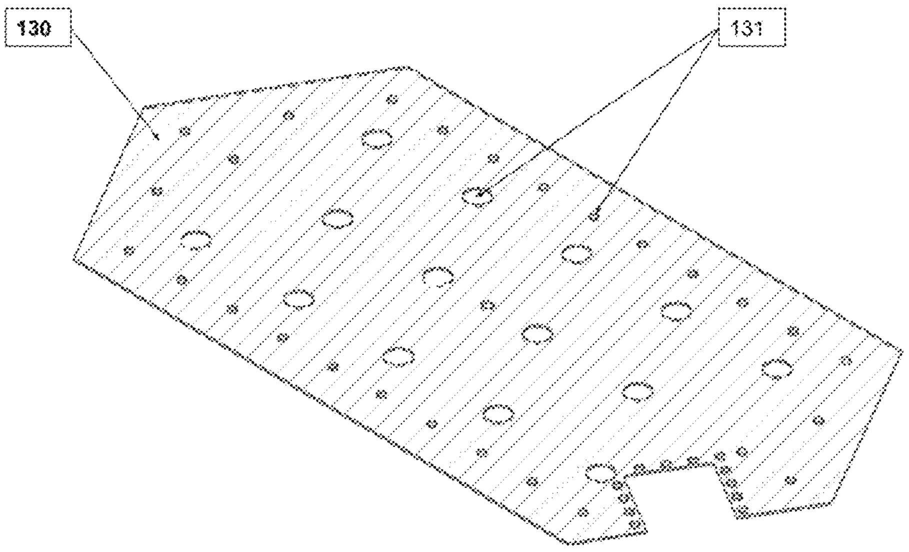
FIG. 2*c* shows the thermal insulation module [130], which allows the heat to be directed mainly towards the contact surface and not towards the outside.

FIG. 2*c* shows the thermal insulation module [130], which allows the heat to be directed mainly towards the contact surface and not towards the outside, it also contains holes that allow elastomer to pass through to ensure mechanical bonding. This module is made or can be made of Mylar or a material of similar behavior.

Figure 2D:
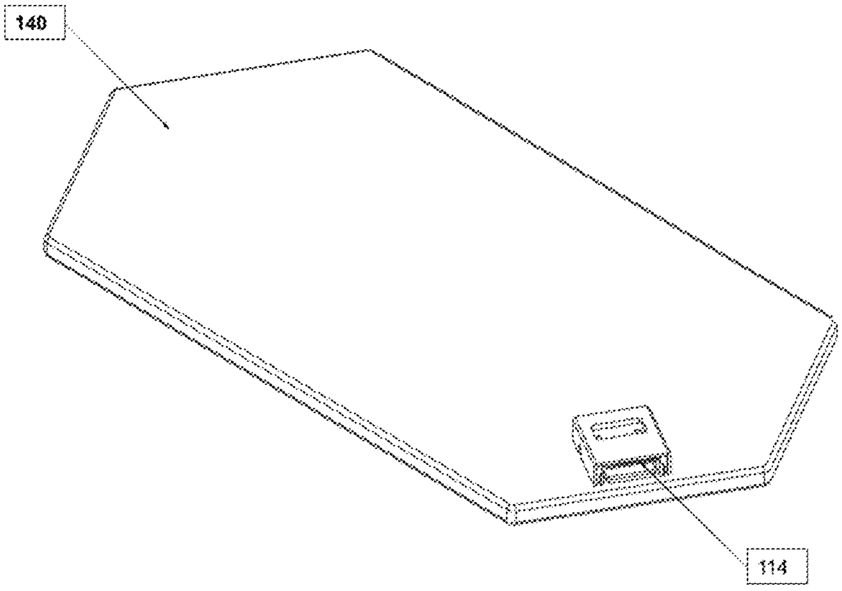
FIG. 2*d* shows the core of the applicator module, which is an elastomer preform that carries inside the three elements shown in FIGS. 2*a*, 2*b* and 2*c*.

The three elements shown in FIGS. 2*a*, 2*b* and 2*c*, are preformed in a mold in which a flexible elastomer is poured, forming the core of the applicator module [100], which is shown in FIG. 2*d*. This process ensures the correct placement of the applicator module components.

Figure 2E:
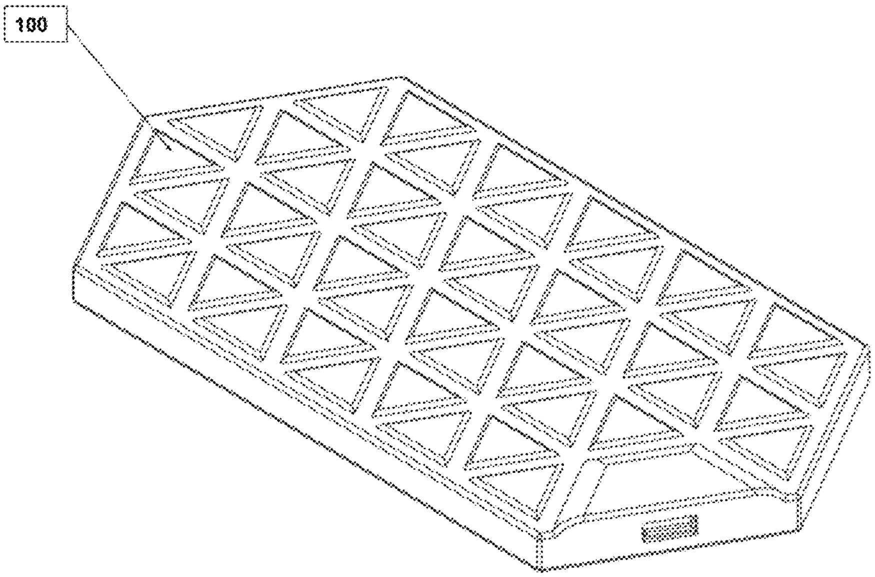
FIG. 2*e* shows the applicator module [100], which results from the encapsulation of the core.

FIG. 2*e* shows the applicator module [100], which results from the encapsulation of the core. The encapsulation process allows to finish the contact layer (which is not visible) and the protective layer, which is the upper surface of the module. This layer has a texture of triangles and allows the protection of the module against wear due to friction or blows. As we mentioned before, the encapsulation is made of a flexible clinical grade elastomer, that is, it can be used in contact with the skin to give therapies in humans, and it encapsulates all the components isolating them from any environmental or electrical exposure.

Figure 2F:
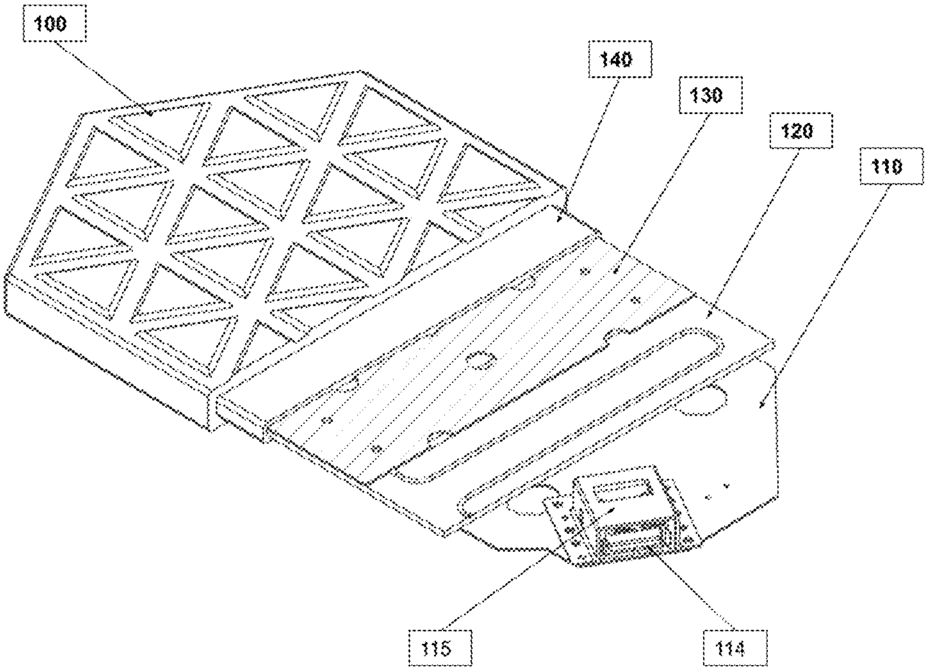
FIG. 2*f* shows a section of the applicator module [100] with all the components of the encapsulation showing their distribution inside.

FIG. 2*f* shows a section of the applicator module [100] with all the components of the encapsulation showing their distribution inside.

Referring to FIG. 1, the control module [200] contains at least one microcontroller [201] in charge of measuring and controlling the therapy time, from the dosage of electrical energy to the infrared and heat energy generator [120] and the infrared emitter [110], responsible for generating infrared and heat energy. The control module [200] also contains power adapters [202] that include a plurality of transistors and electronic components in charge of amplifying the control signals to provide sufficient energy to the infrared and heat energy components. Another component within the control module [200] is the conditioner for temperature sensors [203], which are within the applicator module [100]. Some batteries [204] and some power controllers [205] are also part of the control module, these components are used to provide electrical power to both the control module [200] and the applicator module [100]. Furthermore, this module also includes at least one communication component [207] that includes at least one element for establishing, managing and managing wireless communication and at least one element for remote communication by cable with the thermotherapy system.

Component [208] is a current sensor for heater component [120] and infrared emitter array component [110]. Component [208] allows to perform the tasks of calibration and integrity of the applicator module [100], in addition to that it also performs a sample of the current consumed during the therapy stage to give greater security to the user regarding the correct operation of the applicator module [100], and that if the maximum permitted limits are exceeded, energy will be sent to the patch to avoid damage to the user. During the calibration task, the control module [200] is used to generate the appropriate excitation patterns of the heating components [120] and the array of infrared emitting LEDs [110] contained in the applicator module [100], it will be verified by mean of the temperature sensor component [203] the temperature rise values, the settling times measured by the component [201], the currents through the components [208], the voltage using the characterization provided by the component [204], as well as the amount of watts consumed by the patch to verify that the established excitation parameters are adequate, or failing that, generate those parameters that allow us to obtain the desired calibration results. Furthermore, another task of the control module [200] is the integrity verification of the applicator module [100] which consists of verifying that the values during the calibration stage are not outside the permissible limits and that they indicate a failure due to the possible aging or failure of the applicator module [100], by means of this integrity check it will be possible to detect the possible components that are failing in the modules [100] and [200]. The information generated by the calibration and integrity verification can be sent to the mobile application module [400] and this in turn to the Web application module [600] and the API [500], and therefore can be shared with the user or therapist, in addition to being able to be subjected to data analysis by systems [400], [500] or [600]. Another component is the user interface [206] which consists of several elements (buttons, screen, external connectors) that are shown in FIG. 3*a* and FIG. 3*b*.

Figure 3A:
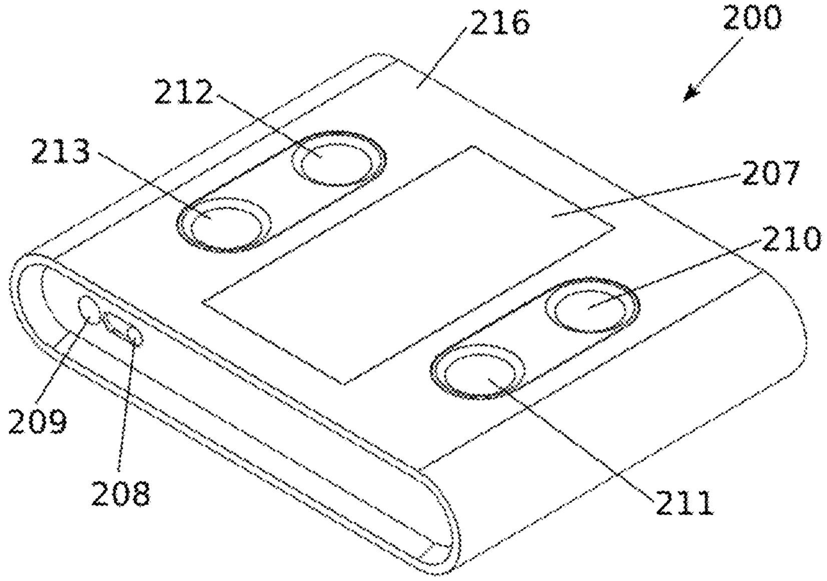
FIG. 3*a* is a lateral top perspective view of the control module of the applicator of FIG. 2, which uses the therapeutic device against musculoskeletal pain of the present invention.
Figure 3B:
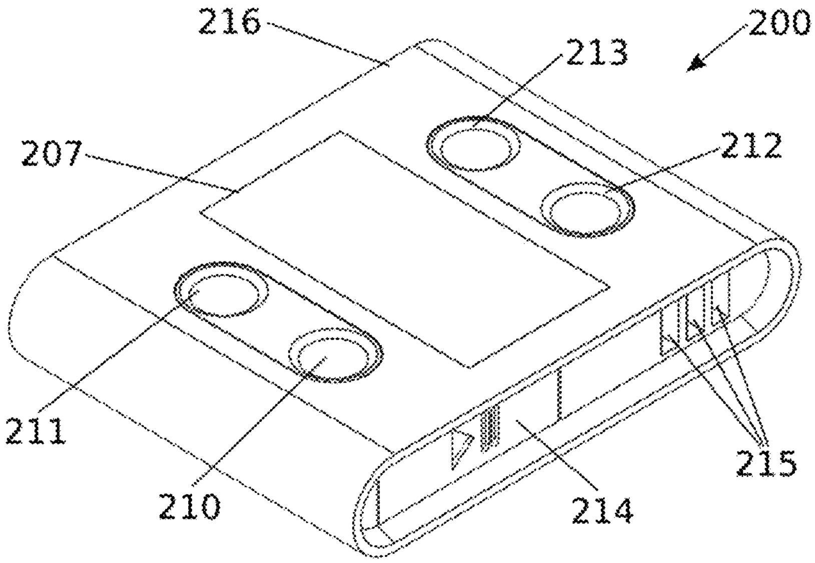
FIG. 3*b* is a lower side perspective view of the module that controls the applicator of FIG. 2 that uses the therapeutic device against musculoskeletal pain of the present invention.
Figure 4:
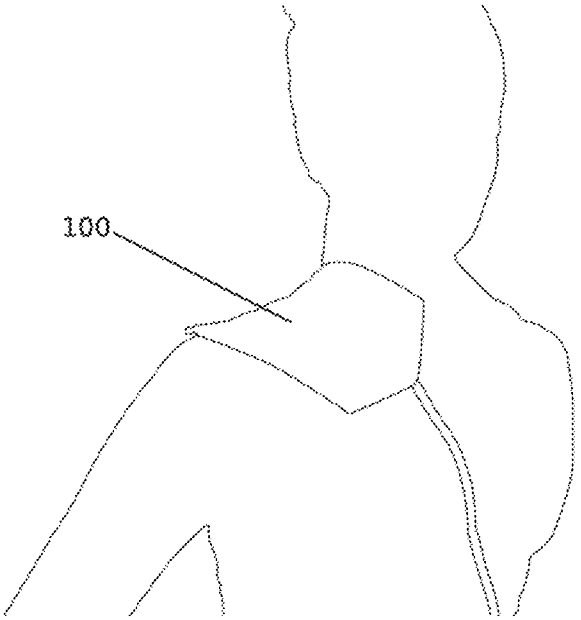
FIGS. 4-6 are views of the mode of use of an application element of the therapeutic device against musculoskeletal pain of the present invention.
Figure 5:
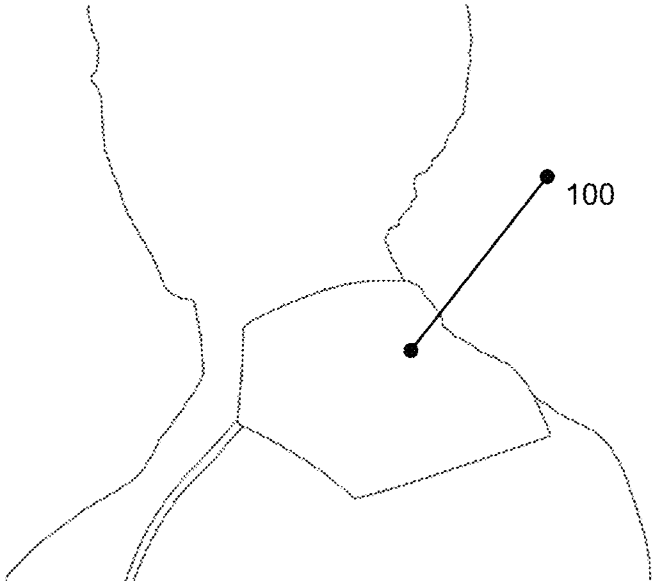
Figure 6:
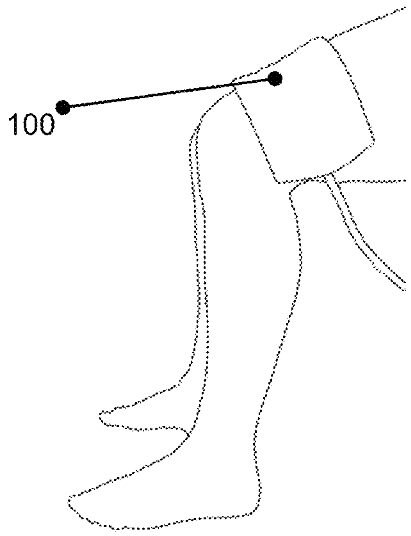
Figure 7:
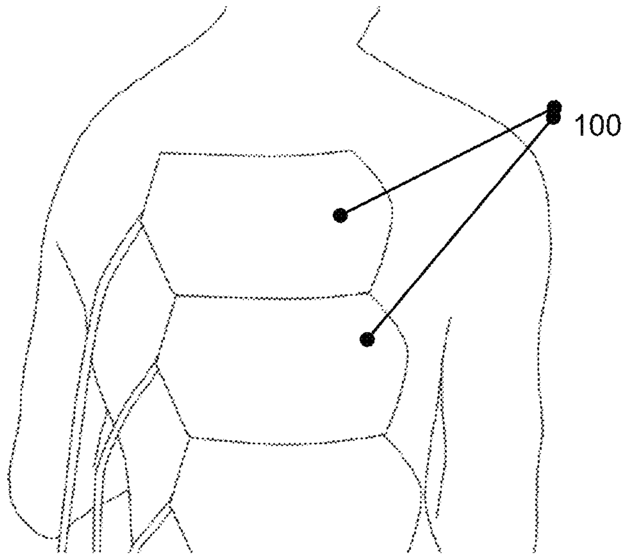
FIG. 7 is a view of the mode of use of various application elements of the therapeutic device against musculoskeletal pain of the present invention.

FIG. 3*a* and FIG. 3*b* show some of the components that make up the control module [200], the design shown is exemplary but not limiting, and which will be detailed below. The control module [200] comprises a screen [207] that provides information to the user, in addition this module can also include a plurality of light elements to satisfy various visual needs such as: warnings, communication establishment, operation, being exemplary but not limiting; a switch [208] used to turn the control module [200] off or on; an input connector [209] for the charger, which is used in order to provide enough energy to charge the batteries [204]; a button [214] that allows the user to start the therapy, if it is already started it will allow him to pause it, and if it is paused it will allow him to continue with it; connectors [215] are for connecting one or a plurality of applicator modules [100] with the control module [200]. The components [215] will allow the control module [200] to include the operation independently of each of the applicator modules [100] with the aim of making irradiances with greater uniformity by means of the infrared emitters arrangement component [110] customized in distributions of intensity patterns and even dynamics, in which the intensity patterns are spatially modified by means of the on-off selection of the applicator modules [100]; or in the same way, perform pain therapy by raising the temperature with greater uniformity or dynamics using the heating component [120] of each of the applicator modules [100]. Component [216] is the control module housing [200].

On the other hand, FIG. 1 shows the mobile application module [300] which contains the components: control logic and analysis [301], the database [302], the user interface component [303] and the Bluetooth communication component [304]. The mobile application module [300] communicates using the Bluetooth communication component [304] with the Bluetooth communication component [207] that is in the control module [200] in order to exchange information and with the possibility of performing control of the system [100] from the mobile application module [300]. On the other hand, the mobile application module [300] will contain a database where the user can create, update or delete information about users, therapies, calibrations, integrity tests and all relevant information generated in the device for transferring heat and infrared energy with dynamic temperature control and homogeneous heat distribution [1000] by the user or during therapies. In addition, the mobile application module contains a user interface component [303] with which the user can interact with the device to transfer heat and infrared energy with dynamic temperature control and homogeneous heat distribution [1000] to control their therapies or receive visual or auditory information about them. The analysis and control tasks within the mobile application module [300] will be carried out by the logic and analysis component [301].

The mobile application module [300] will be able to connect via WIFI to the Internet to establish the data exchange with the control and analysis logic component [401] of the WEB application programming interface (API) module [400]. The API module [400] will obtain the information shared by all users connected through their respective mobile application modules [300], and will save, update or delete them in the database component [402] according to what is indicated by the administrator, using the user interface component [403]. The information that all users share will be saved in the component of a distributed database [402] with which a global analysis of all information within said database can be carried out.

A user or therapist will be able to consult the information of the users or global information, for which they will have limited access, using the WEB application module [500]. The information that the user or therapist can consult via the WEB will be extracted from the database [402] of the WEB API using the communication between the control and analysis logic components [401] and [501]. The therapist or user will communicate with the WEB application module [500] using the user interface component [503]. In addition, any type of local information generated by the interaction of the user or therapist with the WEB application module will be stored locally and if it is considered relevant information, the control and analysis logic component [501] will send it to the WEB API [500] to save it to the global distributed database [502].

FIGS. 4 to 7 show the possible ways in which the user must position himself on the applicator module [100] for pain treatment in the different parts of the body.

Figure 8:
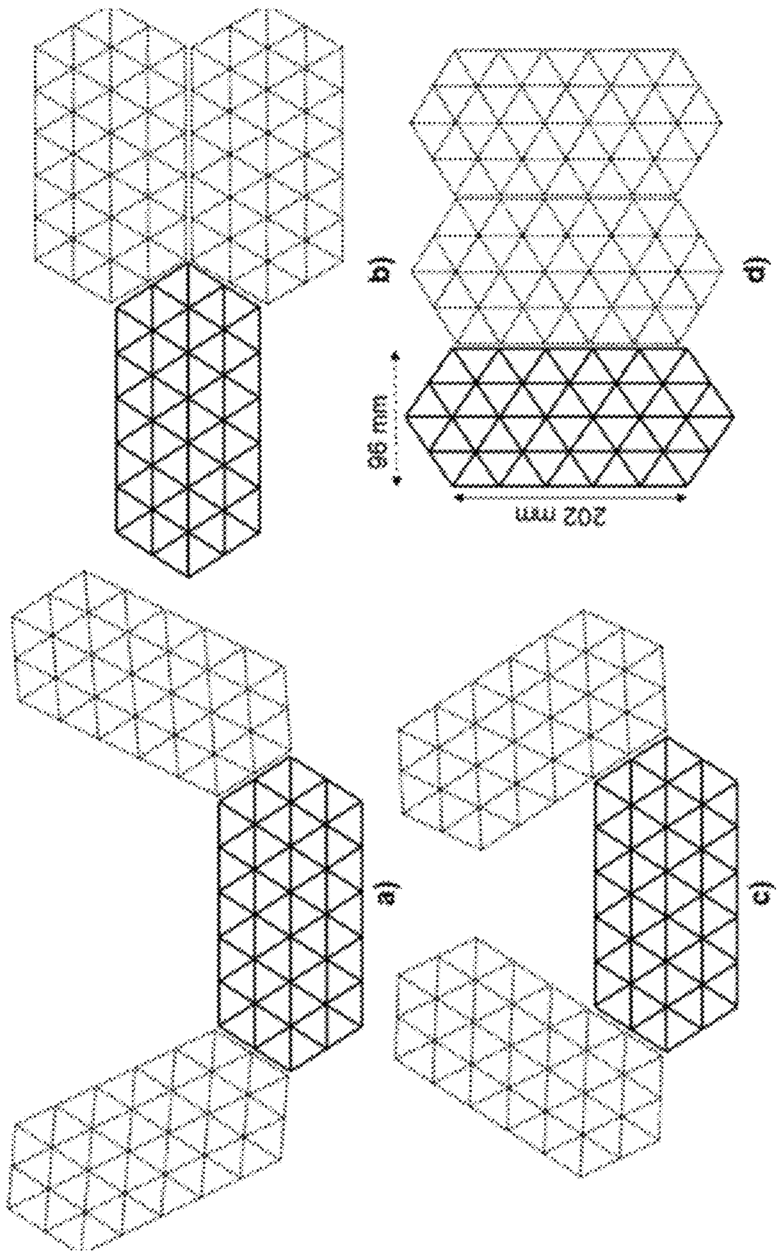
FIG. 8, Possible configurations to use to treat different regions of the body with the heating pad, a) configuration to use to treat the neck-shoulders region, b) configuration used to treat the knee (anterior and posterior), c) setting to treat the knee without involving the patella, d) setting used to treat low back pain.

FIG. 8 shows possible configurations to be used with three applicator modules [100] in different cases.

Figure 9:
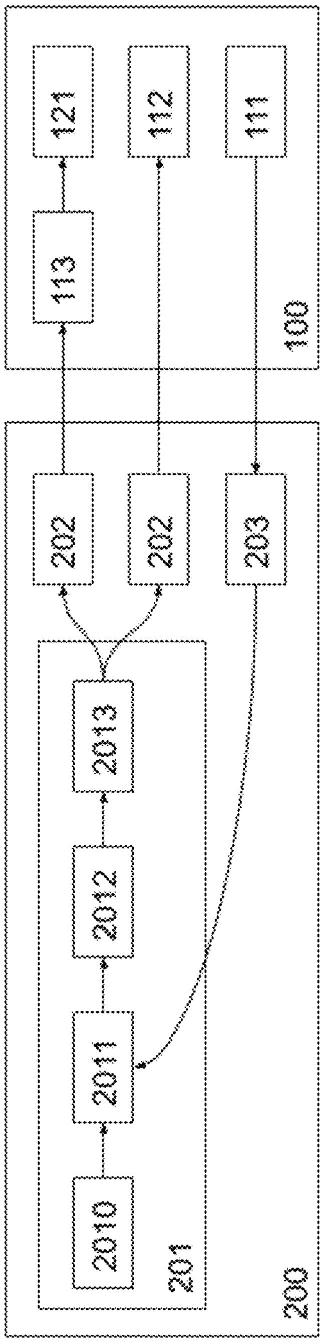
FIG. 9 shows the components contained in the control module [200] that are responsible for temperature control.

Finally, FIG. 9 shows the components contained in the control module [200] that are responsible for temperature control.

Manufacturing Method

In developing the present invention, it is important that the applicator module have its components precisely positioned within the encapsulating means. All these components are also flexible and of irregular geometry, therefore, it must be ensured that their placement is contained in a small volume, otherwise the energy distribution will be irregular and not repeatable in a series of applicator modules.

It is important to mention that elastomers viable for clinical use do not create permanent bonding with any other medium. This led us to the fact that the encapsulation medium had to penetrate and bind with all the components. However, when encapsulating, the viscosity of the elastomer in the injection process did not allow all the components to be encapsulated correctly. In order to obtain a suitable applicator module, a preform was developed that protects the multiple connector and is crimped with the elastomer. Considering that two equal elastomers stick together, when they have the same chemical characteristics, the manufacturing process of the device's applicator module was developed to transfer heat and infrared energy with dynamic temperature control and homogeneous heat distribution, where said process comprises the following stages:

a) All the components to be encapsulated are manufactured, such as the PCB of the Led Light module [110], the heating module [120] and the thermal insulation module [130].
b) A mold is prepared for the applicator module core, which contains structural elements to secure each component in place. The mold contains a series of fastening elements (which can be magnets or presses) strategically placed to secure and compact the components in the vulcanization process. Said structural elements will separate from the core once the elastomer is vulcanized.
c) The pad mold is prepared, which will receive the core. This process allows an injection of the elastomer much more agile and ensuring the placement of all the elements.
d) Open the core mold for component placement.
e) Place the PCB of the Led Light module [110] in the mold.
f) Subsequently insert the heating module [120].
g) Then fit the thermal insulation module [130].
h) Secure and compact all components.
i) Prepare the elastomer and submit it to the vacuum chamber for air removal.
j) Pour the exact amount of elastomer needed to form a core [140].
k) Wait for vulcanization and remove the core [140].
l) Assemble the core in the pad mold.
m) Prepare the elastomer and submit it to the vacuum chamber for air removal.
n) Pour the exact amount of elastomer needed to form the pad.
o) Wait for vulcanization and remove the pad [100].

Therefore, another objective of the present invention is focused on knowing which are the suitable characteristics to generate a therapeutic effect in the various users. That is, it is necessary to know the input parameters (temperatures and application times), as well as the anatomical characteristics of the potential users (for example, the body mass index). This is because the fatty tissue works as an insulating medium, this type of therapy is less effective when applied to areas that have a large amount of accumulated fat. For this reason, studies were carried out to evaluate in a detailed way what happens in those specific cases in order to configure a device that provides the best effect on the user in each individual case. To carry out this validation, models have been made based on the finite element method in 2 and 3 dimensions. Laboratory tests were performed on a pig leg (ex-vivo) with a traditional splint, and subsequently repeated with a prototype of the present invention.

In this context, a first round of models was developed using the finite element method. The results obtained were presented at the XL National Congress of Biomedical Engineering [44]. This article studies the temperature distribution in the body when applying a splint for thermal therapy by means of a parametric study. In this study, the effect of different thicknesses of the fat layer (1 mm-30 mm) when using splints at temperatures ranging from 38° C. to 44° C. was analyzed. The depth of heat penetration was analyzed, as well as the temperatures in the different layers under the application zone. The results suggest that better results are obtained when applying thermal therapy in areas with little fat and at a temperature of 44° C. It is important to mention that grease works as a thermal insulator; therefore, it is necessary to know the level of heat penetration when the thickness of this layer is great. This study focuses mainly on the effect of fat thickness on the results of thermotherapy. The parametric analysis showed that when using a splint at 38° C. it is possible to increase the temperature by 0.5° C. at a depth of 6.45 mm (muscle) when the fat layer is 1 mm thick. On the other hand, by having a 30 mm fat layer with the splint at 38° C., a temperature increase from 0.5° C. to 5.8 mm was achieved. However, this heating occurs only on fat. By increasing the temperature of the splint it is possible to reach higher temperatures and greater depth. It was observed that with a 38° C. splint, a temperature increase of only 0.5° C. was achieved at a depth of 5 mm in muscle (minimum increase considered therapeutic). By increasing the temperature of the splint, the temperature reached at the same 5 mm can reach up to 3.5° C.

It was observed that with a splint at 39° C. for a fat thickness of 1 mm it is possible to achieve temperature increases of 0.5° C. at a depth of approximately 16 mm. When using a splint at 44° C., temperature increases of 1.8° C. were achieved at the same depth of 16 mm. This confirms once again that the temperature of the splint plays a very important role in obtaining therapeutic temperatures.

Even though this is a first approximation of the effect of applying heat through splints at different temperatures, the results obtained showed that the thickness of the fat layer can become a fundamental parameter to achieve a successful therapy or not. That is, with this study it was observed that the results of thermal therapy are mainly dependent on the thickness of the fat in the region to be treated. The thinner the fat, the more successful the heat therapy will be. Using a splint at 44° C. was found to be more efficient; This is due to the fact that temperature increases of up to 4° C. are obtained at depths of 15 mm (above the muscle). In other words, heat not only affects fat tissue, but also directly affects muscle tissue; which would help increase the therapeutic effect of heat.

After the first analysis carried out under this parametric study, the team undertook the task of further investigating the effect of a hot pad (commercial model) in anatomical models [45]. That is, the reconstruction of the cross section of a leg was carried out, on which a hot pad was placed at different temperatures. In this study it was possible to observe the effect of the hot pad on a real anatomical structure. In this study, an analysis was also carried out on the effect of different thicknesses of the fat layer. Additionally, a section of experimental results was included to observe up to what depth level an adequate temperature increase is obtained. In this work, even when a thermal effect was measured at muscle levels, we realized how difficult it is to control a uniform temperature in the pad (commercial device), since it decreases its temperature as a function of the treatment time. This means that the temperature reached at different depths is not maintained for a sufficient time (15 min of treatment).

Over the last months of research, a series of 2D and 3D models of the heating pad have been developed, designed to evaluate its effectiveness in the treatment of musculoskeletal pain. In addition to this modeling stage, work has also been done on the evaluation of the pad in ex vivo pig tissue. The most relevant information obtained in each of these stages is detailed below.

Tool to Parameterize Variables for Effective Thermal Delivery

A series of models were developed to define the appropriate parameters that allow the heating pad to generate a uniform and constant distribution at different depth levels. Most heat pads are not capable of delivering a heat distribution that achieves a sufficient depth of penetration. Therefore, a series of models based on the finite element method was carried out to find out what are the necessary temperatures that the pad must maintain to generate a constant and uniform thermal distribution. In addition, the time that said temperature must be maintained to achieve a minimum temperature increase of 0.5° C. at different depth levels was also analyzed.

3D anatomical models were generated to evaluate the temperature distributions generated by the pad, over the different regions of the body. The effect on the layer of fat, muscles and bone was analyzed. The effect of applying the pad at different temperatures (40° C.-48° C.) and treatment times of 15 min-30 min was also analyzed. The results showed that the thickness of the fat layer is strongly related to the depth of heat penetration and the effectiveness of the therapy. A 44° C. pad temperature was found to be sufficient to treat almost any region of the body, even those with a thicker thickness of fatty tissue.

In thermotherapy, the greatest increase in temperature occurs in the skin and in the subcutaneous tissue (5 mm deep). Therapeutic temperatures at depths around 1.2 cm deep occur slowly and require a longer exposure tune (15-30 min). Here it is important to note that the layer of fat is considered a thermal insulator. Therefore, the tissue under a thick layer of fat is minimally affected by the temperature of applied external agents. Hot compresses between 42° C.-48° C. are the most used in thermotherapy for the treatment of pain. Even high-performance athletes use this type of therapy, due to its high degree of effectiveness. However, the traditional procedure for the application of these hot compresses, even in hospitals, is complicated and ineffective. The inefficiency of these compresses is due to the fact that, in most cases, it is necessary to use thermal baths at very high temperatures to heat the compress to approximately 45° C. Also, it is not possible to keep its temperature constant and uniform throughout heat therapy. That is, the temperature of the compress begins to decrease after a few minutes of starting the treatment. This phenomenon is due to the loss of heat produced by the interaction with the environment.

Therefore, at this stage a specifically designed pad is modeled to maintain a constant and even temperature distribution throughout pain therapy. This is because having a uniform heating would help to ensure that the temperature applied over the entire desired region is the same. Furthermore, this would indicate that the degree of effectiveness of the therapy is due only to the anatomical characteristics of the people under treatment (thickness of their different layers of tissue). The computational models helped to know the parameters (pad temperature and application times) to achieve a uniform heat distribution.

Heating Pad

The size of the pad and its design were chosen in such a way that using only one pad would cover one of the most affected regions (shoulder). The pad of the first prototype used has a width of 96 mm and a length of 202 mm, and its design allows the use of one or a multi-arrangement system of them to cover different sizes of treatment areas. The pad has internally a thermal resistance mesh that maintains its uniform and constant temperature between 40° C.-48° C. (temperature to be chosen by the user) throughout the treatment time (15 min-30 min).

The results of the modeling have helped to conceptualize the therapies that can be given with the heating pad proposed here. However, experimental tests have helped us understand that such a pad is not limited to such an application. The results obtained in the experimentation stage implemented to evaluate the performance of the proposed pad are shown below.

1.—Study of the Eating Uniformity of the Patch.

The pad was operated to assess the uniformity of the heating pattern it generates. For this evaluation, a thermographic camera was used, with which the temperature pattern generated at different instants of time was recorded. Thermal images were recorded from room temperature until it reached a maximum temperature of 57° C. It is important to mention that the temperature of the pad can be set to the desired temperature. It was observed that at the beginning the resistance begins to heat up and a non-uniform pattern is observed; however, after 8 min of ignition, the pattern appears uniform and constant over its entire surface. This study led us to define the optimal resistance per square centimeter used in the present invention and thus to determine the weave pattern in the resistance mesh.

2.—Heating Tests Carried Out with the Heating Pad

Experimental Design

To measure the thermal effect produced by the pad, heating tests were performed on ex-vivo tissue. A pork leg was chosen, since it contained all the layers of tissue necessary to study the thermal effect of the pad; that is, there was a layer of skin, one of fat, and one of muscle. The anatomical specimen had a skin layer of ~1.5 mm, a fat layer with a thick section with a thickness of 18.37 mm; while in its thinnest section its thickness was 3.93 mm. After the fat layer a layer of muscle tissue was found, with a minimum thickness of 30.22 mm and a maximum of 53 mm.

The pig piece was heated to an initial temperature of approximately 37° C. to simulate the physiological temperature of the tissues. Before placing the pad on the surface of the skin, 3 temperature sensors were placed to monitor the increases in temperature on each of the tissue interfaces. That is, the first sensor was placed on the skin-fat interface, the second on the fat-muscle interface; while the last sensor was placed at a depth of 1 cm above the muscle. The sensors were placed in such a way that they were located right in the middle of the pad to be evaluated. In this way, the lateral insertion of each sensor was 52 mm. Once the sensors were placed, the pad under evaluation was mounted on the surface of the skin and fixed in such a way that there was no layer of air between the skin and it.

In the experimental setup used to evaluate the thermal effect generated by the pad on the different layers of tissue, the temperature sensors were located directly on midpoint of the pad. In this case, the pad was preheated (50° C.) at the time it was placed on the pork piece. Although the initial temperature of the pork piece was 37° C., the piece of pork lowered its temperature by approximately 3° C., while the temperature sensors and the pad were placed. The pad was turned off after 30 min of operation; on the skin-fat interface, a temperature increase of approximately 10° C. was observed; the fat-muscle interface showed a temperature increase of 3.5° C.; while at a depth of 1 cm above the muscle an increase of approximately 1° C. was achieved. With this experiment, it was observed that indeed the pad under evaluation is capable of generating an increase in temperature capable of generating a therapeutic effect at the muscular level.

One of the most relevant experiments was the one that helped to verify that the design heating pad is capable of generating uniform thermal distributions at different depth levels. In this case, the experiment was carried out using a pork leg at room temperature (26° C.). In this experiment the tissue layers were removed; that is, the skin, fat and muscle layers were obtained separately. To perform the heating test, the pad was placed on the worktable, then the skin layer (2.74 mm), the first sensor, the fat layer (9 mm), the second sensor and finally the muscle layer was placed. A third temperature sensor was inserted into the muscle layer approximately 24.6 mm deep.

In the same way, it is observed how the temperature of the pad increases as a function of time. The temperature of this was set at 50° C.; therefore, once that temperature is reached, the controller kicks in and keeps it uniform for the rest of the time. It is observed how the desired temperature is reached at approximately 30 min. On the other hand, the sensor on the skin registered a $\Delta T=16.5°$ C. the fat showed a $\Delta T=6.5°$ C. while in the muscle at an approximate depth of 24.6 mm a $\Delta T\sim1°$ C. was achieved. This indicates that the pad is capable of achieving sufficient depth of penetration to achieve a local therapeutic effect on the muscle area.

However, the most important part was observing that the pad is capable of generating uniform heating over the different layers of fabric. The thermal image shows two markers in which it is observed that both the fat layer and the muscle reached temperatures of approximately 34.3° C., which indicates a $\Delta T=10°$ C. on the fat-muscle interface. The temperature distribution over fat and skin, in this case, both markers show a temperature of 44.9° C. The pad is capable of generating a uniform thermal distribution, not only over the skin layer, but over all the tissue layers analyzed. It is also observed how the temperature manages to pass the fat layer (9 mm thick and is evenly distributed over the muscle layer. Furthermore, it was observed that in approximately 30 min a $\Delta T\sim0.5°$ C. is reached at depths less than 1 cm deep in muscle.

It is important to mention that both the modeling stage and the ex vivo experimentation stage have helped to define the appropriate parameters for the pad to be able to generate a constant and uniform temperature distribution as a function of time. In addition, to be able to achieve sufficient depth of penetration to achieve a minimum temperature increase of 0.5° C. at deeper levels. These experiments also made it possible to define the calibration method and continuous temperature monitoring to achieve the expected results.

The following table shows the measurements of one of the experiments, it is shown how the muscle temperature increases more than 1.5° C. in thirty minutes of therapy:

| | Time | Skin (2.74 mm) | Fat (9 mm) | Muscle 1 cm | Pad | Environment |
|---|---|---|---|---|---|---|
| ON | 0:00:00 | 32.4 | 33.8 | 36.6 | | 25.7 |
| | 0:01:00 | 32.8 | 34.1 | 36.6 | 33.50 | 25.7 |
| | 0:02:00 | 33.4 | 34.2 | 36.6 | 36.30 | 25.7 |
| | 0:03:00 | 34.3 | 34.3 | 36.7 | 38.50 | 25.7 |
| | 0:04:00 | 35.2 | 34.5 | 36.7 | 40.48 | 25.7 |
| | 0:05:00 | 36.2 | 34.8 | 36.7 | 42.40 | 25.7 |
| | 0:06:00 | 37.2 | 35.1 | 36.7 | 43.90 | 25.7 |
| | 0:07:00 | 38.1 | 35.4 | 36.7 | 45.56 | 25.7 |
| | 0:08:00 | 39.1 | 35.8 | 36.7 | 46.60 | 25.7 |
| | 0:09:00 | 40.0 | 36.1 | 36.8 | 47.90 | 25.7 |
| | 0:10:00 | 40.9 | 36.6 | 36.8 | 47.02 | 25.7 |
| | 0:11:00 | 41.1 | 37.0 | 36.9 | 48.93 | 25.7 |
| | 0:12:00 | 42.3 | 37.4 | 37.0 | 49.66 | 25.7 |
| | 0:13:00 | 42.8 | 37.7 | 37.0 | 50.10 | 25.7 |
| | 0:14:00 | 43.3 | 38.1 | 37.1 | 48.80 | 25.7 |
| | 0:15:00 | 43.7 | 38.4 | 37.2 | 49.70 | 25.7 |
| | 0:16:00 | 44.1 | 38.7 | 37.2 | 48.83 | 25.7 |
| | 0:17:00 | 44.4 | 39.0 | 37.3 | 49.30 | 25.7 |
| | 0:18:00 | 44.7 | 39.3 | 37.4 | 49.30 | 25.7 |
| | 0:19:00 | 45.0 | 39.5 | 37.5 | 48.25 | 25.7 |
| | 0:20:00 | 45.3 | 39.7 | 37.6 | 48.26 | 25.7 |
| | 0:21:00 | 45.6 | 39.9 | 37.6 | 48.26 | 25.7 |
| | 0:22:00 | 45.8 | 40.1 | 37.7 | 49.38 | 25.7 |
| | 0:23:00 | 45.9 | 40.3 | 37.8 | 49.44 | 25.7 |
| | 0:24:00 | 46.1 | 40.3 | 37.9 | 49.30 | 25.7 |
| | 0:25:00 | 46.2 | 40.7 | 38.0 | 49.09 | 25.7 |
| | 0:26:00 | 46.4 | 40.8 | 38.0 | 49.57 | 25.7 |
| | 0:27:00 | 46.6 | 40.9 | 38.0 | 49.68 | 25.7 |
| | 0:28:00 | 46.8 | 41.1 | 38.1 | 49.51 | 25.7 |
| | 0:29:00 | 46.8 | 41.2 | 38.1 | 49.23 | 25.7 |
| | 0:30:00 | 47.0 | 41.4 | 38.2 | 49.56 | 25.7 |
| | 0:31:00 | 47.1 | 41.5 | 38.2 | 50.60 | 25.7 |
| | 0:32:00 | 47.2 | 41.5 | 38.3 | 49.44 | 25.7 |
| | 0:33:00 | 47.3 | 41.7 | 38.4 | 49.51 | 25.7 |
| | 0:34:00 | 47.4 | 41.8 | 38.4 | 49.41 | 25.7 |
| | 0:35:00 | 47.4 | 41.9 | 38.4 | 49.37 | 25.7 |
| | 0:36:00 | 47.5 | 42.0 | 38.4 | 49.40 | 25.7 |
| | 0:37:00 | 47.6 | 42.0 | 38.5 | 49.93 | 25.7 |
| | 0:38:00 | 47.6 | 42.0 | 38.5 | 49.70 | 25.7 |
| | 0:39:00 | 47.7 | 42.2 | 38.5 | 48.67 | 25.7 |
| | 0:40:00 | 47.8 | 42.2 | 38.6 | 49.15 | 25.7 |
| | 0:41:00 | 47.9 | 42.3 | 38.6 | 48.70 | 25.7 |
| | 0:42:00 | 47.9 | 42.4 | 38.6 | 49.22 | 25.7 |
| | 0:43:00 | 48.1 | 42.4 | 38.7 | 48.95 | 25.7 |
| | 0:44:00 | 18.1 | 42.5 | 38.7 | 49.26 | 25.7 |
| | 0:45:00 | 48.2 | 42.5 | 38.7 | 49.45 | 25.7 |
| | 0:46:00 | 48.2 | 42.7 | 38.7 | 49.79 | 25.7 |
| | 0:47:00 | 48.3 | 42.7 | 38.7 | 48.80 | 25.7 |
| | 0:48:00 | 48.4 | 42.7 | 38.7 | 49.10 | 25.7 |
| | 0:49:00 | 48.4 | 42.8 | 38.8 | 49.20 | 25.7 |
| | 0:50:00 | 48.4 | 42.9 | 38.8 | 49.33 | 25.7 |
| | 0:51:00 | 48.5 | 42.9 | 38.8 | 49.58 | 25.7 |
| | 0:52:00 | 48.6 | 43.0 | 38.8 | 49.60 | 25.7 |
| | 0:53:00 | 48.6 | 43.0 | 38.9 | 49.68 | 25.7 |
| | 0:54:00 | 48.5 | 43.1 | 38.9 | 49.60 | 25.7 |
| | 0:55:00 | 48.5 | 43.1 | 38.9 | 49.67 | 25.7 |
| | 0:56:00 | 48.5 | 43.1 | 38.9 | 49.95 | 25.7 |
| | 0:57:00 | 48.6 | 43.1 | 38.9 | 48.68 | 25.7 |
| | 0:58:00 | 48.6 | 43.2 | 38.9 | 49.44 | 25.7 |
| | 0:59:00 | 48.6 | 43.2 | 39.0 | 49.62 | 25.7 |
| | 1:00:00 | 48.6 | 43.3 | 39.0 | 49.13 | 25.7 |

The present invention also provides an operating process of the device for transferring heat and infrared energy with dynamic temperature control and homogeneous heat distribution [1000], which comprises the following stages, which will be described based on the diagram in FIG. 1:

A) Calibration. To achieve that the device transfers infrared and heat energy in a homogeneous way, and repeatability was achieved, a calibration stage is required. This stage involves the use of the applicator module [100] and the control module [200] in conjunction with a surface temperature measurement device, which can be from a thermometer, a thermocouple or a thermographic camera. The process described below involves the surface heat generation calibration of the applicator module [100]. For this, the maximum surface temperature of the applicator module [100] is measured with one of the measurement devices mentioned above, on the surface that will be in contact with the user of the device [1000], once the stable temperature state has been reached for a fixed PWM value by the microcontroller component [201] of the control module [200]. The temperature measured by component [111] should also be recorded. This procedure is carried out for different PWM values to obtain a table of: each one of the PWM values of the microcontroller [201], maximum surface temperature of the applicator module [100] registered with the temperature sensor [111] ($T_s$) maximum temperature measured on the surface of the applicator module with a calibrated temperature measuring aid ($T_m$). From these measurements a mathematical model is obtained where we will obtain $T_s$ of a temperature chosen by the user $T_m$. Through this step it is sought that different applicators [100] generate a similar heat for a temperature set by the controller [200], since due to small differences in manufacturing and properties of the applicators [100], both mechanical and electronic components, can cause differences in heat generation that must be compensated. With this model it is possible to obtain the temperature to be measured by the sensor $T_s$ given a fixed surface temperature $T_m$.

B) Execution of Therapy. The main component of the control module that is responsible for executing the therapy is the microcontroller component [201]. The microcontroller [201] requires a control model that depends on the temperature measured by the sensor $T_s$ and a reference temperature. The reference temperature is obtained from the model obtained in the calibration stage. The description of the present stage is based on FIG. 9 which is an enlargement of FIG. 1 to explain said stage. The components contained in the control module [200] that are responsible for temperature control are: a fixed temperature component [2010]; a temperature comparing element [2011], which compares the temperature obtained by the temperature sensors [111] contained in the applicator component [100] and adapted by means of the component [203]; an adaptation and control element [2012] which can be from a PID (proportional integral derivative) control element, some variation of this, or any type of control of the same nature that is capable of performing temperature compensation tasks; the component [2013] is a PWM (Pulse Width Modulation) type modulator, which encodes the signals into the appropriate forms to finally send them to component [202] which is in charge of performing the power coupling in order to inject enough energy to the heating element [121] and infrared LEDs [112] to raise its temperature to the appropriate value.

C) User Feedback. The user receives feedback about the therapies through the screen in the user interface [206], included in the control component [200]. The information it provides to the user is about: the temperature registered by the sensors [111] of the applicator module [100], the time remaining for the therapy to finish, the temperature that the user set for the applicator module [100].

D) Improvement and personalization of therapies. In the event that the user requires any modification of the temperature of the therapy or the duration of the therapy, it can be done by means of the buttons contained in the user interface [206] of the control module [200]. This therapy customization will be saved in the microcontroller [201] and it will be sent to the mobile application module [300] and through the Web API [400] to the Web application [500] which will allow the analysis of the information about the modifications that users make to therapies. This information will be used to generate improvements and new proposals for therapies for different regions of the body that will be sent through updates to the control module [200], through the mobile application [300].

E) Data analytics. The data analysis will be carried out through the Web API [400] and the Web application [500], using the information provided and generated by the user from the control module [200] and mobile application [300], which includes information about therapies, treatment region, and user information that is useful for the therapist, and for improving therapies, based on statistics, for example, on body mass index and age. The information generated could also help to generate statistics on different problems that users of the device have.

The invention claimed is:

1. A device for transferring heat and infrared energy with dynamic temperature control and homogeneous heat distribution, comprising:

at least one applicator module (100);

a first discrete layer comprising a PCB (110) comprising temperature sensors (111), infrared energy generating system instrumentation (112), and a thermoelectric safety component (113), each connected via electrical connection tracks to a multiple connector, wherein the infrared energy generating system instrumentation comprises an infrared emitter (112) comprising LEDs configured to emit infrared radiation between 800 and 1200 nm by converting electrical energy to IR radiation;

a second discrete layer comprising a heating module (120) comprising a resistance mesh embedded in an elastomer and connected via electrical connection tracks to the multiple connector, wherein the heating module receives electrical energy to generate heat, and the generated heat is directed toward a contact surface of the applicator module;

a third discrete layer comprising a thermal insulation module (130) formed of a heat-directing material;

a core (140) that comprises the elastomer and encapsulates the first layer, the second layer, and the third layer, the elastomer coupling the PCB (110), the heating module (120) and the thermal insulation module (130), the core (140) being encapsulated within the applicator module (100); and a control module (200) including electronics for power and temperature regulation.

2. The device to transfer heat and infrared energy with dynamic temperature control and homogeneous heat distribution as claimed in claim 1, wherein the heating module (120) is composed of the resistance mesh (121) woven on a wire mesh, the resistance mesh bonded with the elastomer that forms the core (140) of the applicator module (100).

3. The device to transfer heat and infrared energy with dynamic temperature control and homogeneous heat distribution as claimed in claim 1, wherein the temperature sensors (111) will allow the control module (200) to know a temperature in real time at various points of the applicator module (100) which will allow the control module (200) to manage the energy supplied to the heating module (120).

4. The device to transfer heat and infrared energy with dynamic temperature control and homogeneous heat distribution as claimed in claim 1, wherein the thermal insulation module (130) contains holes, the elastomer passing through the holes to ensure a mechanical joint, and the thermal insulation module made of a material that directs heat generated by the heating module towards a contact surface of the applicator module.

5. The device to transfer heat and infrared energy with dynamic temperature control and homogeneous heat distribution of claim 1, further comprising:

a wireless communication component within the control module;

a mobile application module (300) comprising a user interface component, a control logic, a wireless communication component, and a database component;

a web application programming interface module (400) comprising a communication logic, a data management, and an administrative interface; and a web application module (500) configured to visualize synchronized therapy data.

6. The device to transfer heat and infrared energy with dynamic temperature control and homogeneous heat distribution as claimed in claim 5, wherein the mobile application module (300) communicates using the wireless communication component (304) with the wireless communication component (207) that is in the control module (200) in order to exchange information and with the possibility of controlling the applicator module (100) from the mobile application module (300).

7. The device to transfer heat and infrared energy with dynamic temperature control and homogeneous heat distribution as claimed in claim 5, wherein the web application programming interface module (400) will obtain information shared by connected users through their respective mobile application modules (300), and will save, update, or delete the information in the database component (402) according to what is indicated by an administrator, using the user interface component (403), and wherein the information that users share is stored in the distributed database (402) with which a global analysis of information within said distributed database can be carried out.

8. The device to transfer heat and infrared energy with dynamic temperature control and homogeneous heat distribution as claimed in claim 1, further comprising one or more additional applicator modules identical or equivalent to the first applicator module, wherein each applicator module is operatively connected to the control module and configured to operate simultaneously with the others.

9. The device to transfer heat and infrared energy with dynamic temperature control and homogeneous heat distribution as claimed in claim 4, wherein upon heating, the resistance mesh maintains a uniform and constant temperature across its surface.

10. The device to transfer heat and infrared energy with dynamic temperature control and homogeneous heat distribution as claimed in claim 9, wherein the uniform and constant temperature is between 40° C. and 45° C.

11. The device to transfer heat and infrared energy with dynamic temperature control and homogeneous heat distribution as claimed in claim 1, wherein the heating module receives electrical energy from the control module.

12. The device to transfer heat and infrared energy with dynamic temperature control and homogeneous heat distribution of claim 1, wherein the second layer is arranged on top of the first layer, and the third layer is arranged on top of the second layer.

13. A manufacturing process of a device to transfer heat and infrared energy with dynamic temperature control and homogeneous heat distribution, comprising the following stages:

a) manufacturing components to be encapsulated to form a core, the core configured to be further encapsulated within an applicator module, the components comprising:

a first discrete layer comprising a PCB with an LED light module (110);

a second discrete layer comprising a heating module (120) comprising a resistance mesh configured to receive electrical energy to generate heat; and a third discrete layer comprising a thermal insulation module (130), the thermal insulation module formed of a heat-directing material;

b) preparing a core mold configured to receive the components for forming the core of the applicator module;

c) preparing a pad mold;

d) placing the PCB with the LED light module (110) into the core mold;

e) subsequently placing the heating module (120) into the core mold;

f) then placing the thermal insulation module (130) into the core mold;

g) pouring an amount of elastomer into the core mold sufficient to encapsulate the components to form the core (140);

h) waiting for vulcanization and removing the core (140) from the core mold;

i) placing the core into the pad mold;

j) pouring the amount of elastomer into the pad mold sufficient to form the applicator module; and k) waiting for vulcanization and removing the applicator module from the pad mold.

14. The manufacturing process of claim 13, wherein the thermal insulation module (130) comprises holes, and wherein pouring an amount of the elastomer into the core mold further comprises allowing the elastomer to pass through the holes and mechanically bond with the resistance mesh of the heating module (120).

15. The manufacturing process of claim 13, wherein the first layer comprising the PCB (110) is placed into the core mold before the second layer comprising the heating module (120), and the second layer is placed before the third layer comprising the thermal insulation module (130).

16. The manufacturing process of claim 13, further comprising submitting the elastomer to a vacuum chamber for air removal prior to pouring the elastomer into the core mold and prior to pouring the elastomer into the pad mold.

17. The manufacturing process of claim 13, further comprising securing the PCB (110), the heating module (120), and the thermal insulation module (130) in position within the core mold before pouring the elastomer.

18. The manufacturing process of claim 13, wherein preparing the core mold includes providing at least one fastening element configured to hold the PCB (110), the heating module (120), and the thermal insulation module (130) in position during formation of the core.

* * * * *